United States Patent [19]
Furusawa et al.

[11] Patent Number: 6,059,720
[45] Date of Patent: May 9, 2000

[54] ENDOSCOPE SYSTEM WITH AMPLIFICATION OF FLUORESCENT IMAGE

[75] Inventors: Koichi Furusawa; Atsumi Kaneko, both of Tokyo, Japan

[73] Assignee: Asahi Kogaku Kogyo Kabushiki Kaisha, Tokyo, Japan

[21] Appl. No.: 09/035,337

[22] Filed: Mar. 5, 1998

[30] Foreign Application Priority Data

Mar. 7, 1997  [JP]  Japan ................................. 9-053622

[51] Int. Cl.⁷ .......................................... A61B 1/04
[52] U.S. Cl. ........................ 600/160; 600/109; 348/76
[58] Field of Search ........................ 600/109, 160; 348/65, 76, 300

[56] References Cited

U.S. PATENT DOCUMENTS

| | | | |
|---|---|---|---|
| 4,791,480 | 12/1988 | Muranaka | 358/65 |
| 4,951,135 | 8/1990 | Sasagawa et al. | 348/65 |
| 4,967,269 | 10/1990 | Sasagawa et al. | 348/65 |
| 5,078,150 | 1/1992 | Hara et al. | |
| 5,162,913 | 11/1992 | Chatenever et al. | 358/65 |
| 5,452,723 | 9/1995 | Wu et al. | |
| 5,507,287 | 4/1996 | Palcic et al. | |
| 5,701,903 | 12/1997 | Sano et al. | |
| 5,749,830 | 5/1998 | Kaneko et al. | 600/109 |

FOREIGN PATENT DOCUMENTS

| | | |
|---|---|---|
| 6-54792 | 3/1994 | Japan. |
| 7155292 | 6/1995 | Japan. |
| 7-77580 | 8/1995 | Japan. |
| 7204156 | 8/1995 | Japan. |
| 8224210 | 9/1996 | Japan. |

*Primary Examiner*—John P. Leubecker
*Attorney, Agent, or Firm*—Greenblum & Bernstein, P.L.C.

[57] ABSTRACT

An endoscope system is provided with an endoscope unit which emits an excitation light to an object to be observed and receives a fluorescent light emitted by the object, a filtering optical element, which extracts a predetermined component of the fluorescent light received by the endoscope unit, an image capturing device, which receives an image formed by the predetermined component of the fluorescent light, an amplifier, which amplifies an output signal of the image capturing device, and a gain controller, which automatically controls a gain of the amplifier in accordance with the output signal of the image capturing element.

5 Claims, 10 Drawing Sheets

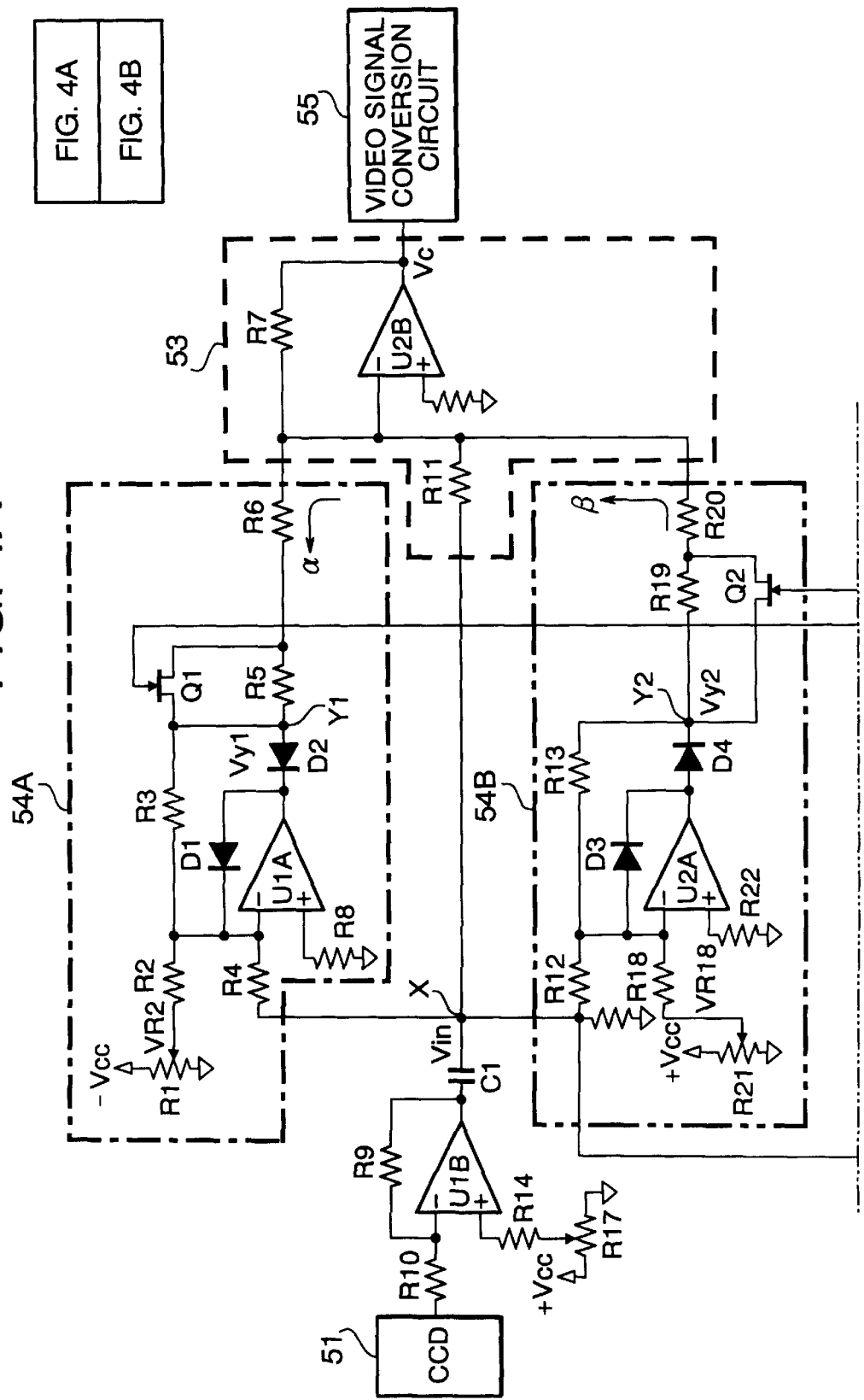

ENDOSCOPE SYSTEM WITH AMPLIFICATION OF FLUORESCENT IMAGE

BACKGROUND OF THE INVENTION

The present invention relates to an endoscope system for observing a fluorescing object, and more particularly to an endoscope system which emits excitation light towards an object to be observed, receives a fluorescent light emitted by the object, and display an image of the fluorescing object.

It has been known that, when organic tissues are illuminated by light having wavelengths of 420 nm through 480 nm, fluorescent substances included in the organic tissues such as NAHD, FMN fluoresce. By observing an image of the fluorescing organic tissues, a disorder of the organic tissue can be found. Specifically, light fluoresced by normal (i.e., not diseased) organic tissues includes more green component than a red component, while light fluoresced by organic tissues having a disorder includes less green component than the red component. Thus, based on the amount of the green fluorescent light, whether the organic tissues has a disorder can be determined.

The amount of the fluorescent light, however, varies depending on a distance between the organic tissue and a distal end of the endoscope. For example, if the distal end of the endoscope is relatively close to organic tissues having a disorder, the amount of the fluorescent light may be as much as that of organic tissues which do not have a disorder.

In order to avoid such a deficiency, in an endoscope utilizing the fluorescent light, diagnosis may be done based on a ratio of the green component of the fluorescent light to the red component.

In order to obtain the ratio of the green component to the red component, however, an imaging unit is required to include color filters for separating the red and green components from the fluorescent light, a pair of image intensifiers for the red and green components, and a pair of CCDs (Charge Coupled Devices) for the red and green components. Due to such a structure, the imaging unit becomes relatively large in size, and heavy, which lowers an operability of the endoscope. Further, due to a large number of elements, the endoscope utilizing the fluorescent light tends to be expensive.

SUMMARY OF THE INVENTION

It is therefore an object of the invention to provide an improved endoscope system utilizing the fluorescent light which enables accurate diagnosis regardless of the distance between the object (e.g., the organic tissues) and the distal end of the endoscope, and further the imaging unit thereof can be made compact.

For the object, according to the invention, there is provided an endoscope system for observing an image of a fluorescing object, comprising: an endoscope unit which emits an excitation light to an object to be observed and receives a fluorescent light emitted by the object; a filtering optical element, which extracts a predetermined component of the fluorescent light received by the endoscope unit; an image capturing device, which receives an image formed by the predetermined component of the fluorescent light; an amplifier, which amplifies an output signal of the image capturing device; and a gain controller, which automatically controls a gain of the amplifier in accordance with the output signal of the image capturing element.

Since the gain of the amplifier is controlled based on the image signal output by the image capturing device, an appropriate signal can be obtained even though the distance between the distal end of the endoscope and the organic tissues to be observed is not appropriate, and/or the light illuminating the object is not appropriate.

In particular, the gain controller increases the gain of the amplifier when the output of the image capturing device is within a predetermined value range.

Optionally or alternatively, it is preferable that the gain controller decreases the gain of the amplifier when the output of the image capturing device is out of a predetermined value range.

Further, the endoscope system may be provided with a discriminating system which determines one of a plurality of value ranges in which the output of the image capturing is included, and wherein the gain controller determines the gain of the amplifier based on a value range is which the output of the image capturing included.

Still optionally, the predetermined component may be a light having a wavelength within a range of 500 nm through 570 nm.

According to another aspect of the invention, there is provided an endoscope system for observing an image of a fluorescing object, comprising: an endoscope unit which emits an excitation light to an object to be observed and receives a fluorescent light emitted by the object; a filtering optical element, which extracts a predetermined component of the fluorescent light received by the endoscope unit; an image intensifier which amplifies an intensity of a received light; an image capturing device, which receives an image formed by the predetermined component of the fluorescent light, the image intensifier being provided in front of the image capturing device; a driver which controls a gain of the image intensifier; and controller, which controls a gain of the image intensifier in accordance with the output signal of the image capturing device.

Optionally, the driver changes gain of the image intensifier by changing a voltage applied to the image intensifier.

In this case, the controller controls the driver to decrease the voltage when output of the image capturing device outputs a signal having a value within a predetermined value range.

Further, the controller controls the driver to increase the voltage when output of the image capturing device outputs a signal having a value out of a predetermined value range.

Optionally, the controller controls the gain of the image intensifier based on a peak value of output signal of the image capturing device within a predetermined period.

Still optionally, the gain controller changes the gain of the image intensifier only when the peak value of the output signal is greater than a predetermined reference peak value.

Furthermore, the predetermined period corresponds to a period in which the image capturing device output the signal for one frame.

According to further aspect of the invention, there is provided an endoscope system for observing a fluorescent image, comprising: an endoscope unit which emits an excitation light to an object to be observed and receives a fluorescent light emitted by the object; a filtering optical element, which extracts a predetermined color component of the fluorescent light received by the endoscope unit; an image capturing device, which receives an image formed by the predetermined color component of the fluorescent light and outputs an image signal; and a variable gain amplifier, a gain of which changes in accordance with the image signal output by the image capturing device.

Optionally, the variable gain amplifier may compare the image signal output by the image capturing device with a plurality of reference values defining a plurality of signal level ranges, and wherein the gain of the variable gain amplifier is changed stepwisely in accordance with a signal level range in which the image signal is included.

In particular, the variable gain amplifier may include: a first amplifying circuit which amplifies the output signal of the image capturing device and outputs a first output signal, the first output signal fluctuates with respect to a predetermined value; a second amplifying circuit which amplifies the first output signal at a predetermined gain and outputs a second output signal; a first circuit which compares the first output signal with a first higher reference value which is higher than the predetermined value, the first circuit lowering the gain of the second amplifying circuit if the first output signal has a higher value than the first higher reference value; a second circuit which compares the first output signal with a first lower reference value which is lower than the predetermined value, the second circuit lowering the gain of the second amplifying circuit if the first output signal has a lower value than the first lower reference value.

Further optionally, the variable gain amplifier further may include: a third circuit which compares the first output signal with a second higher reference value which is higher than the first higher reference value, the third circuit further lowering the gain of the second amplifying circuit if the first output signal has a higher value than the second higher reference value; and a fourth circuit which compares the first output signal with a second lower reference value which is lower than the first lower reference value, the fourth circuit lowering the gain of the second amplifying circuit if the first output signal has a lower value than the second lower reference value.

DETAILED DESCRIPTION OF THE PREFERRED EMBODIMENTS

Figure 1:
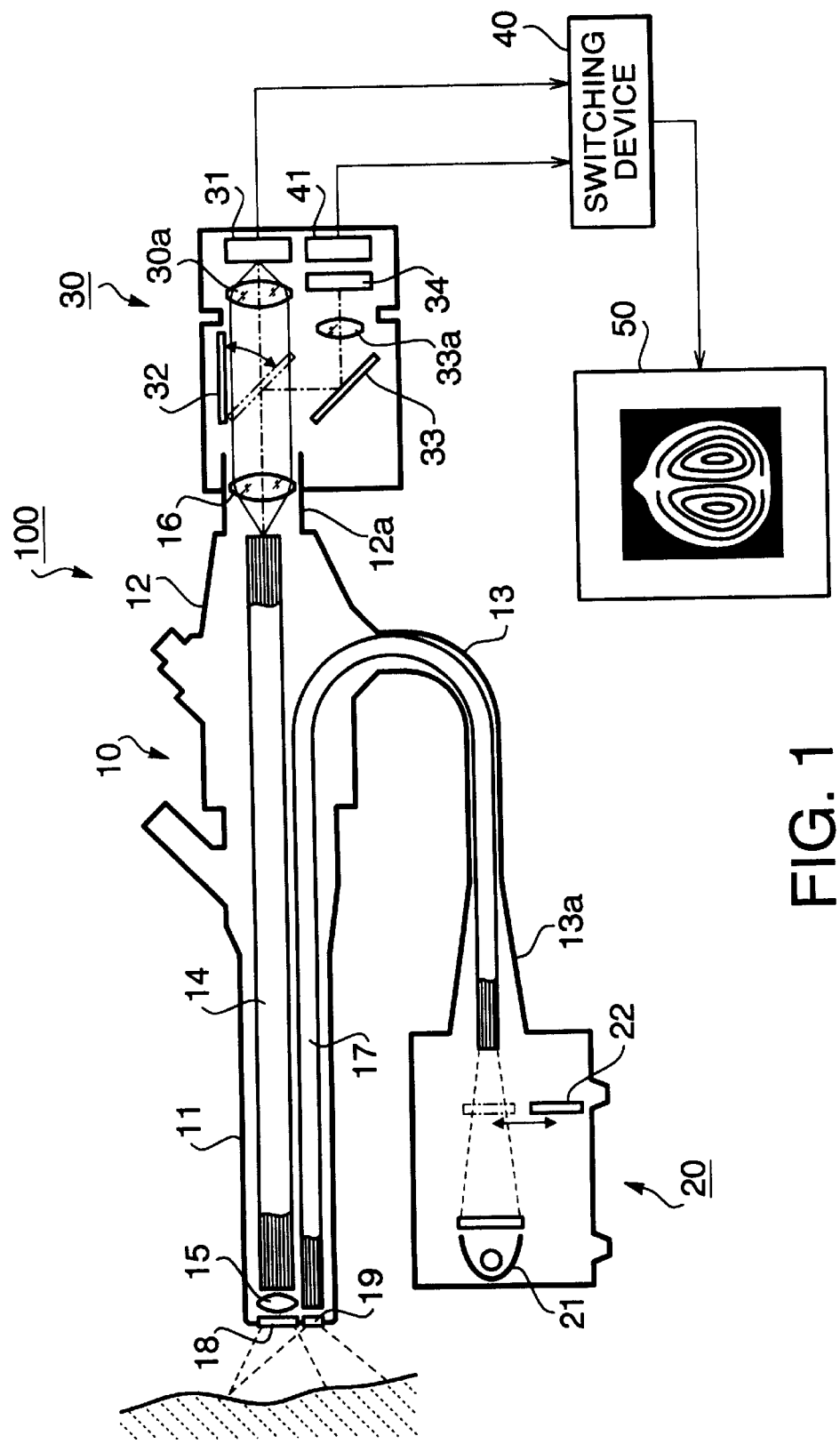
FIG. 1 shows a schematic structure of an endoscope system according to a first embodiment of the invention.

FIG. 1 shows a structure of an endoscope system 100 according to a first embodiment of the invention. The endoscope system 100 includes an endoscope 10, a light source unit 20 which emits light for illuminating an object to be observed, and an imaging unit 30 for capturing image of the object. A display device 50 is connected to the imaging unit 30 via a video switching device 40.

As shown in FIG. 1, the endoscope 10 has insertion portion 11 having a cylindrical shape, an operation portion 12 which is connected to a proximal end of the insertion portion 11, and a light guide connecting tube 13 which is formed as an extension of the outer surface of the operation portion 12. The operation portion 12 is provided with an eyepiece unit 12a by which the endoscope 10 and the imaging unit 30 are detatchably connected. At a distal end of the light guide connecting tube 13, a connector 13a is provided. The endoscope 10 is detatchably connected to the light source unit 20 by means of the connector 13a.

As shown in FIG. 1, an image guide fiber bundle 14 is enclosed, in the endoscope 10, from the distal end of the insertion portion 11 to the proximal end of the operation portion 12. Inside the distal end of the insertion portion 11, an objective optical system 15 which forms an image of the object on a light receiving end surface of the image guide fiber bundle 14 is accommodated. On the side end of the insertion portion 11 at a position corresponding to the objective optical system 15, a window 18 is formed to introduce light from the object towards the objective optical system 15.

In the eyepiece unit 12a, an eyepiece lens 16 is accommodated for observing the image which is guided from the light receiving end surface to a light emerging end surface of the image guide fiber bundle 14. It should be noted that the eyepiece lens 16 is usually used such that an observer can view the image therethrough. However, if the imaging unit 30 is connected as shown in FIG. 1, the eyepiece lens 16 is moved to a position corresponding to 0 (zero) diopter. The light emitted by the object located in front of the distal end of the endoscope 10 is introduced inside the endoscope 10, and converged by the objective optical system 15. The image formed by the objective optical system 15 is transmitted by the image guide fiber bundle 14 towards the eyepiece unit 12a, and then introduced to the imaging unit 30 through the eyepiece lens 16.

Inside the endoscope 10, from the end of the connector 13a to the distal end of the insertion portion 11, a light guide fiber bundle 17 is provided. A light receiving surface (i.e., a connector 13a side surface) of the light guide fiber bundle 17 faces the light source unit 20 when the connector 13a is connected to the light source unit 20. An light emerging surface (i.e., a distal end side surface) of the light guide fiber bundle 17 is arranged perpendicular to an optical axis of the objective optical system 17. In front of the light guide fiber bundle 17, on the end surface of the endoscope 10, a window 19 is formed.

Inside the light source unit 20, a Xenon lamp 21 is provided at a position opposing to the light guide fiber bundle 17 when the connector 13a is connected to the light source unit 20. When the Xenon lamp 21 emits light, the light is converged and incident on the light receiving surface of the light guide fiber bundle 17. The light is then transmitted inside the light guide fiber bundle 17 and emerged from the other end of the light guide fiber bundle 17, and emitted outside through the window 19.

A filter 22 for excitation light is movably provided such that the filter 22 can be inserted in or retracted from an optical path between the lamp 21 and the light receiving surface of the light guide fiber bundle 17, by means of a solenoid (not shown). The filter 22 is inserted in the optical path when the fluorescent image is to be observed, and is retracted from the optical path when a normal image is observed. The filter 22 allows light having a wavelength within a range of 420 nm through 480 nm. The organic tissues, when illuminated with the excitation light having the wavelength of 420 nm through 480 nm, fluoresce and emit light. Normal organic tissues (which do not have disorder) fluoresce and emit light having a wavelength within a range of 500 nm through 570 nm. The fluorescent light emitted by the organic tissues pass through the observing window 18, the objective optical system 15, and incident on the light receiving surface of the image guide fiber bundle 14.

The imaging unit 30 accommodates an imaging optical system 30a which constitutes, together with the eyepiece lens 16, a relay optical system. At a position where the imaging optical system 30a forms an image, a CCD camera 31 for normal observation is disposed. Further, as shown in FIG. 1, another CCD camera 41 for observing fluorescent light image is disposed next to the CCD camera 31. In this embodiment, the CCD camera 31 and the CCD camera 41 have the same structure. The CCD cameras 31 and 41 are connected to a switching device 40 which is connected to the display device 50. The switching device 40 transmits one of the signals output by the CCD camera 31 and CCD camera 41 to the display device 50.

Between the CCD camera 31 and the eyepiece lens 16, a mirror 32 which is retractably inserted in the optical path between the eyepiece lens 16 and the CCD camera 31 is provided. The mirror 32 deflects the light emerged from the eyepiece lens 16 when inserted within the optical path. When the normal observation is performed, the mirror 32 is retracted from the optical path as indicated by a solid line in FIG. 1. When the fluorescent image is to be observed, the mirror 32 is inserted in the optical path. In this case, the optical axis of the eyepiece lens 16 intersects the reflection surface of the mirror 32 at 45 degrees as indicated by broken lines in FIG. 1 such that light emerged from the eyepiece lens 16 is deflected at 90 degrees.

On the optical axis of the eyepiece lens 16 deflected by the mirror 32, a dichroic mirror 33 is provided such that the optical axis intersects the reflection surface of the dichroic mirror 33 at 45 degrees. The dichroic mirror 33 reflect light having a wavelength within a range of 500 nm through 570 nm, and allows the other light to pass through.

On the optical path of the light reflected by the dichroic mirror 33, an imaging optical system 33a is provided, and at a position where an image is formed by the imaging optical system 33a, an image intensifier 34 for amplifying an intensity of light reflected by the dichroic mirror 33 is provided. It should be noted that an optical path length between the eyepiece lens 16 and the CCD camera 31 and an optical path length between the eyepiece lens 16 and the image intensifier 34 are the same.

Figure 2:
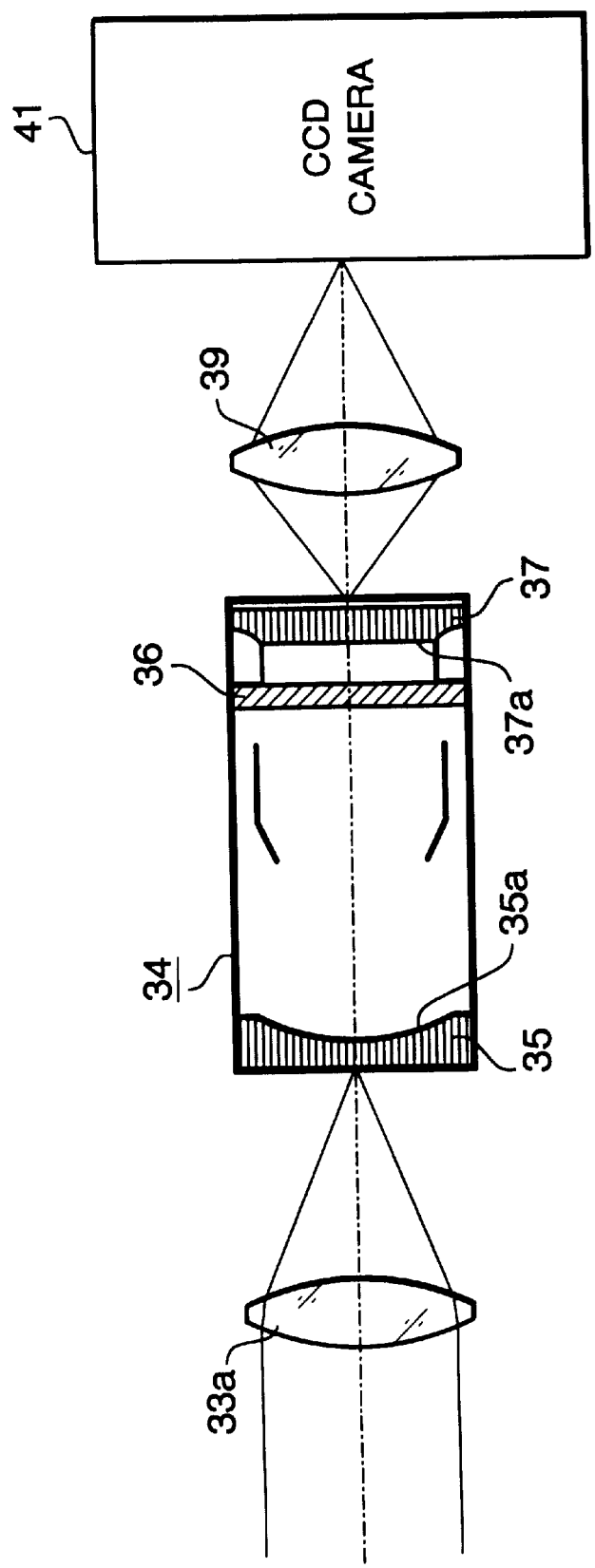
FIG. 2 schematically shows a structure of an image intensifier employed in the endoscope system shown in FIG. 1.

FIG. 2 schematically shows a structure of the image intensifier 34. In FIG. 2, the image intensifier 34 includes a first fiber plate 35 having a photo-electrical surface 35a, a micro channel plate (MCP) 36, and a second fiber plate 37 which has a fluorescent surface 37a. When an image of the organic tissues is formed on the first fiber plate 35 by the imaging optical system 33a, the first fiber plate 35 divides the formed image into pixels and transmits the pixels, and transmits the light to the photo-electrical surface 35a. The photo-electric surface 35a thus converts the optical image into an electronic image. On both sides of the MCP 36, electrodes are connected to which a predetermined voltage is applied. Thus, the electronic image converted by the photo-electric surface 35a is amplified when passes through the MCP 36, and is projected on the fluorescent surface 37a at which the electronic image is converted into an optical image. The converted optical image is transmitted to an opposite side surface of the second fiber plate 37. As above, the fluorescent object image amplified by the image intensifier 34 is relayed by the imaging optical system 39 provided on the light emerging surface side of the image intensifier 34, and is incident on the CCD camera 41 for observing the fluorescent image.

Figure 3:
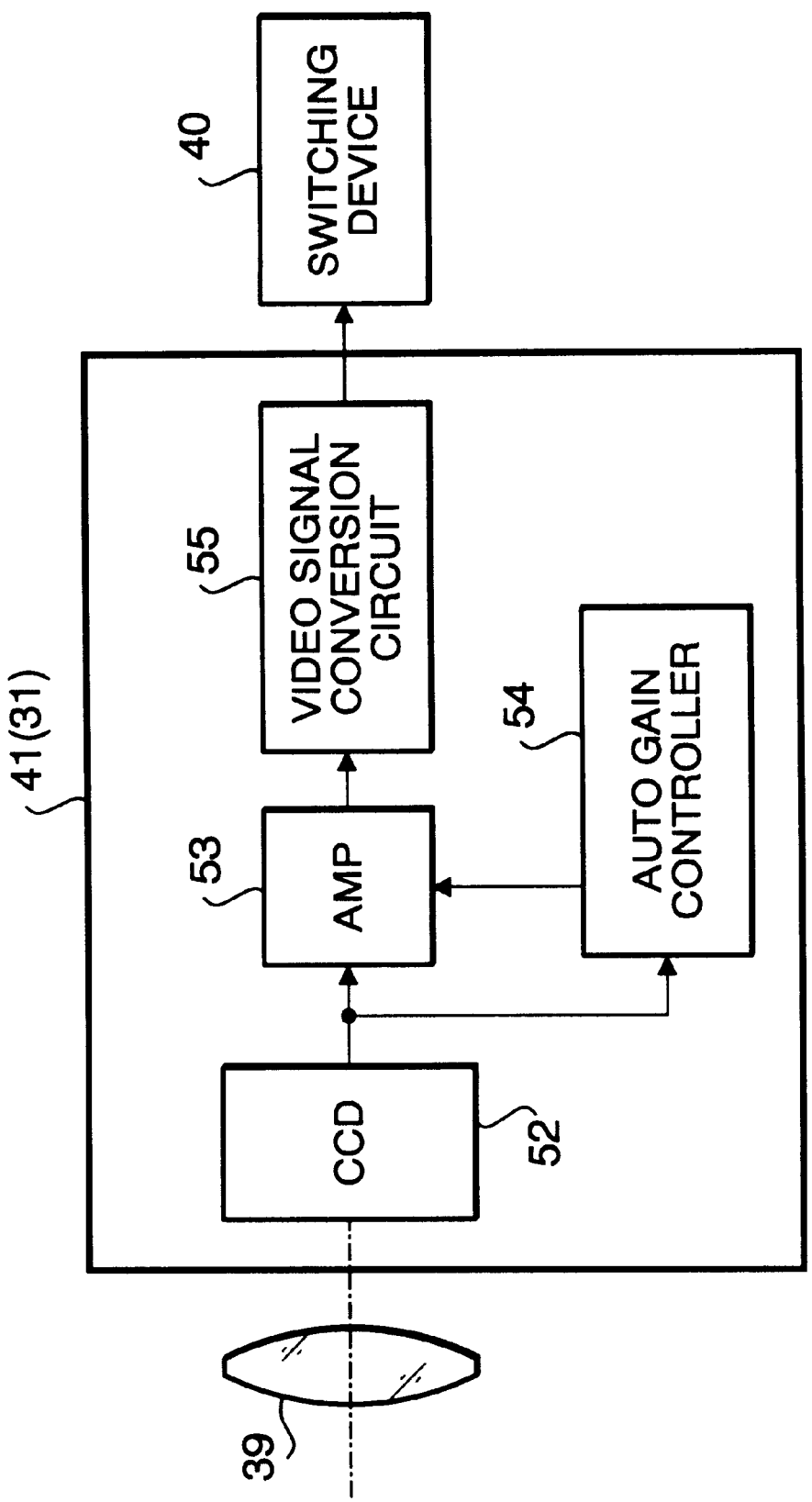
FIG. 3 a block diagram of a CCD camera unit used in the endoscope shown in FIG. 1.

FIG. 3 is a block diagram illustrating the CCD camera 41. As shown in FIG. 3, the CCD camera 41 includes a CCD (Charge Coupled Device) 51, an amplifier 53 for amplifying an output signal of the CCD 51, an automatic gain controller (AGC) 54 which controls a gain of the amplifier 53, and a video signal conversion circuit 55 for converting the output signal of the amplifier 53 into a video signal.

CCD 51 is an area sensor for receiving the image output from the light emerging surface of the image guide fiber bundle 14. The CCD 51 is arranged such that the light receiving surface of the CCD 51 is substantially perpendicular to the optical axis of the imaging optical system 39. The output signal of the CCD 51 is input to the amplifier 53 and the AGC 54.

The amplifier 53 amplifies the signal output by the CCD 51 at a certain gain, the transmits the amplified signal to the video signal conversion circuit 55. In this embodiment, the gain of the amplifier 53 is variable, and is controlled by the AGC 54.

The AGC 54 controls the gain of the amplifier 53 based on the amplitude of the CCD 51 so that the output signal of the amplifier 53 has a value within a predetermined range. That is, if the amplitude of the signal supplied from the CCD 51 to the AGC 54 is greater than a predetermined reference value (e.g., if a distance between the distal end of the endoscope 10 and the object to be observed is shorter than an appropriate distance, or intensity of excitation light illuminating the object is larger than an appropriate amount), the AGC 54 lowers the gain of the amplifier 53. On the other hand, if the amplitude of the signal supplied from the CCD 51 to the AGC 54 is less than the predetermined reference value (e.g., if a distance between the distal end of the endoscope 10 and the object to be observed is greater than the appropriate distance, or intensity of excitation light illuminating the object is less than the appropriate amount), the AGC 54 increases the gain of the amplifier 53.

The video signal conversation circuit 55 receives the output signal of the amplifier 53 and converts the received signal into the video signal (e.g., an NTSC signal), and transmits the converted signal to the switching device 40.

Figure 4B:
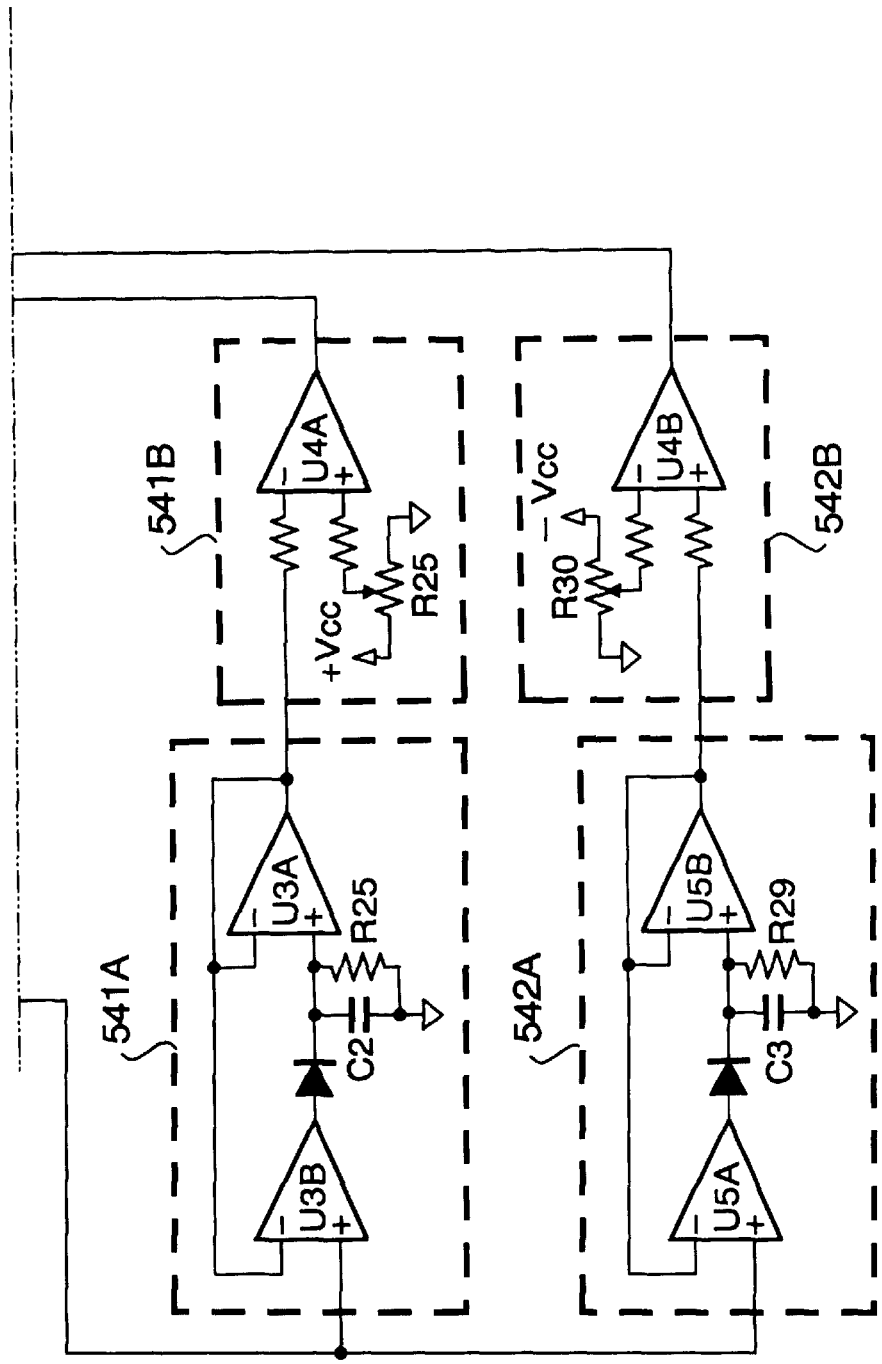
FIG. 4 (which consists of FIGS. 4A and 4B) shows a circuitry of the CCD camera unit shown in FIG. 3.

FIGS. 4A and 4B shows a circuitry of the CCD camera 41.

An output terminal of the CCD 41 is connected, through a resistor R10 to an inverting input terminal of the operational amplifier U1B. A non-inverting input terminal of the operational amplifier U1B is connected, through a resistor R14 and a variable resistor R17, to a voltage source Vcc. A feed back resistor R9 connects the output terminal and the inverting input terminal of the operational amplifier U1B. Further, the output terminal of the operation amplifier U1B is connected with a condenser C1 for preventing a DC component from being transmitted. The other end of the condenser C1 is connected to a resistor R16 for discharging the condenser C1. With this construction, a DC (direct current) component of the output signal of the CCD 51 is removed by the condenser C1.

The end of the condenser C1 at which the resistor R16 is connected, is also connected, through a resister R11, to the inverting input terminal of an operational amplifier U2B.

The non-inverting input terminal of the operational amplifier U2B is connected to an end of a resistor R15, the other end of which is grounded. A feed back resistor R7 connects the output terminal and the inverting input terminal of the operational amplifier U2B. The output of the operational amplifier U2B is input to the video signal conversion circuit 55.

Figures 5A, 5B:
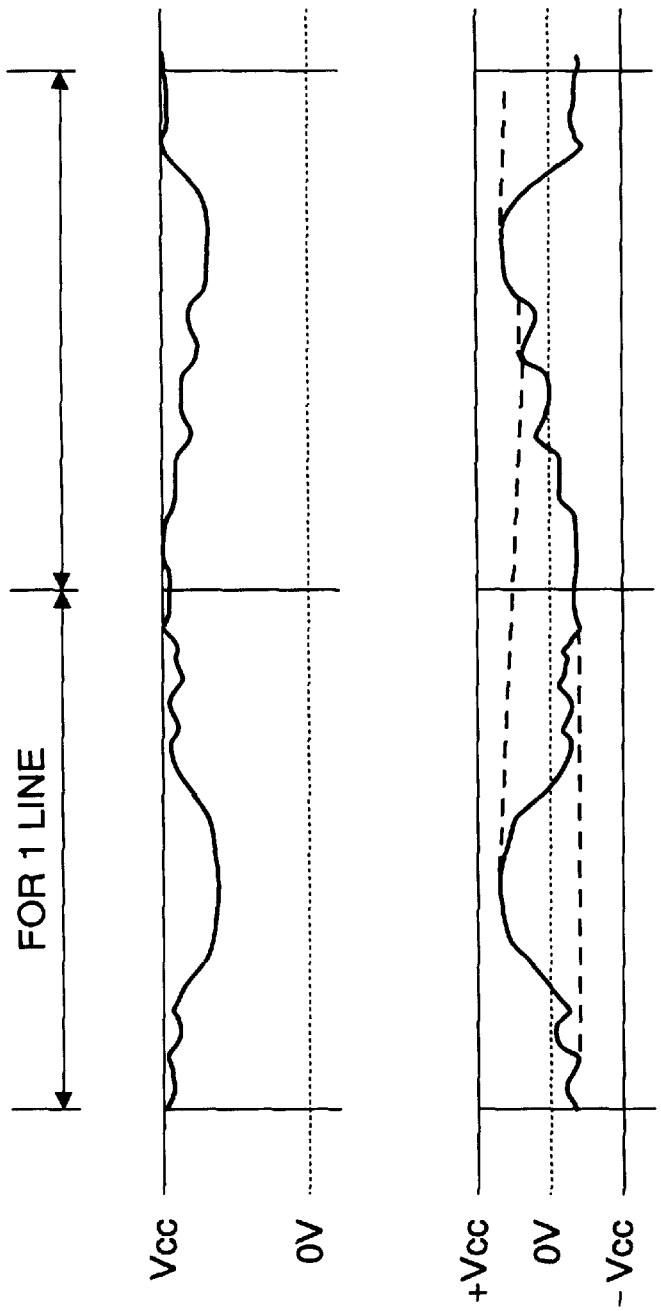
FIGS. 5A and 5B show wavelength of an output signal of the CCD shown in FIG. 3.

An example of change of the output voltage of the CCD 51 (i.e., a voltage applied to the inverting input terminal of the operational amplifier U1B) is shown in FIG. 5A. The output voltage is lowered, with respect to a predetermined voltage, i.e., Vcc, in accordance with amount of light received by the CCD 51. The output voltage of the CCD 51 is inverted and amplified by the operational amplifier U1B, and output thereby. The output voltage of the operational amplifier U1B is applied, through the condenser C1, at a point X in FIG. 4A, and an example thereof, which corresponds to the output voltage of the CCD 51 shown in FIG. 5A is indicated in FIG. 5B. The voltage at the point X is inverted and amplified by the operational amplifier U2B, the output voltage of which is applied to the video signal conversation circuit 55.

If the output voltage of the operational amplifier U2B is less than a first predetermined negative reference value, an output value control circuit 54A, which is indicated by one-dotted lines in FIG. 4A, functions to substantially lower the gain of the operational amplifier U2B. The output value control circuit 54A is described in detail hereinafter.

The point X is connected to the inverting input terminal of the operational amplifier U1A. The inverting input terminal of the operational amplifier U1A is also connected with a resistor R2 and a variable resistor R1 which is connected to a constant voltage source. The non-inverting input terminal of the operational amplifier U1A is connected to a resistor R8 the other end of which is grounded. Between the output terminal and the inverting input terminal of the operational amplifier U1A, a diode D1 is connected. Further, to the output terminal of the operational amplifier U1A, a diode D2, a resistor R5, and a resistor R6 are connected in series. The end of the resistor R6 is connected to resistor R7 and the inverting input terminal of the operational amplifier U2B. At a point where the resistor R2 is connected to the inverting input terminal of the operational amplifier U1A, an end of the resistor R3 is connected, the other end of the resistor R3 is connected to the diode D2 and a source of an FET Q1. A gate of the FET Q1 is connected to the output terminal of a comparator 541B. The source of the FET Q1 is connected to a connecting point Y1 of the resistor R5 and the diode D2, and a drain of the FET Q1 is connected to the other end of the resistor R5. It should be noted that the FET Q1 is turned On or OFF by the comparator 541B which will be described in detail.

With this construction, the output voltage of the output voltage control circuit 54A is 0 (zero) volt when the voltage output by the operational amplifier U1B is negative. To the resistor R2, a negative reference voltage VR2 is applied. Therefore, if the absolute value of the voltage (a positive voltage Vin at the point X) applied to the resistor R2 is smaller than the negative reference voltage VR2, the diode D1 is forward-biased and the diode D2 is reverse-biased, and accordingly the operational amplifier U1A does not amplify the input voltage. If the absolute value of the positive voltage Vin is greater than the absolute value of the negative reference voltage VR2, the diode D1 is reverse-biased, and accordingly an electrical current flows across the resistors R3 and R4. In this case, the operational amplifier U1A invert-amplifies the input voltage applied to the inverting input terminal at a predetermined gain. It should be noted that, by changing the value of the variable resistor R1 to change the voltage VR2, the characteristic of the output value control circuit 54A can be changed.

Similar to the above, if the output voltage of the operational amplifier U2B is greater than a first positive reference value, an output value control circuit 54B, which is indicated by two-dotted lines in FIG. 4A, functions to substantially lower the gain of the operational amplifier U2B. The output value control circuit 54B is now described in detail hereinafter.

The point X is connected to the inverting input terminal of the operational amplifier U2A through a resister R12. The inverting input terminal of the operational amplifier U2A is also connected with a resistor R18 and a variable resistor R21 which is connected to a positive constant voltage source. The non-inverting input terminal of the operational amplifier U2A is connected to a resistor R22 the other end of which is grounded. Between the output terminal and the inverting input terminal of the operational amplifier U2A, a diode D3 is connected. Further, to the output terminal of the operational amplifier U2A, a diode D4, a resister R19, and a resister R20 are connected in series. The end of the resistor R20 is connected to resistor R7 and the inverting input terminal of the operational amplifier U2B. At a point where the resistor R18 is connected to the inverting input terminal of the operational amplifier U2A, an end of the resistor R13 is connected, the other end of the resistor R13 is connected to the diode D4 and a source of an FET Q2. A gate of the FET Q2 is connected to the output terminal of a comparator 542B. The source of the FET Q2 is connected to a connecting point Y2 of the resistor R19 and the diode D4, and a drain of the FET Q2 is connected to the other end of the resistor R19. It should be noted that the FET Q2 is turned ON or OFF by the comparator 542B which will be described in detail.

With this construction, the output voltage of the output voltage control circuit 54B is 0 (zero) V when the voltage output by the operational amplifier U1B is positive. To the resistor R18, a positive reference voltage VR18 is applied. Therefore, if the voltage Vin at the point X is negative and the absolute value of the voltage Vin is smaller than the positive reference voltage VR18, the diode D3 is forward-biased and the diode D4 is reverse-biased, and accordingly the operational amplifier U2A does not amplify the input voltage. If the absolute value of the negative voltage Vin is greater than the absolute value of the positive reference voltage VR18, the diode D3 is reverse-biased, and accordingly an electrical current flows across the resistors R18 and R13. In this case, the operational amplifier U2A invert-amplifies the input voltage applied to the inverting input terminal at a predetermined gain. It should be noted that, by changing the value of the variable resistor R21 to change the voltage VR18, the characteristic of the output value control circuit 54B can be changed.

In the circuitry shown in FIGS. 4A and 4B, a voltage Vc at the output terminal C of the operational amplifier U2B is expressed as follows.

$$Vc=-(Vc1+Vc2+Vc3) \quad (1)$$

In equation (1), voltage Vc1 represents an output voltage of the operational amplifier U2B based only on the output voltage of the operational amplifier U1A, and is expressed as follows:

$$Vc1=-Vy1\times(R7/R5+R6)) \quad (2),$$

where Vy1 is a voltage at the point Y1.

In equation (1), voltage Vc2 is an output voltage of the operational amplifier U2B based only on the output voltage of the operational amplifier U1B, and is expressed as follows:

$$Vc2=-Vx \times (R7/R11) \qquad (3),$$

where Vx is the voltage at the point X (i.e., Vx=Vin).

In equation (1), voltage Vc3 is an output voltage of the operational amplifier U2B based only on the output voltage of the operational amplifier U2A, and is expressed as follows:

$$Vc3=-Vy2 \times (R7/R19+R20)) \qquad (4),$$

where Vy2 is a voltage at the point Y2.

Accordingly, the operational amplifier U1A varies a negative electrical current α (indicated in FIG. 4A) so that the voltage applied to the inverting input terminal of the operational amplifier U2B to vary.

Similarly, the operational amplifier U2A varies a positive electrical current β (indicated in FIG. 4A) so that the voltage applied to the inverting input terminal of the operational amplifier U2B to vary.

The AGC 54 further includes, as shown in FIG. 4B, a first peak hold circuit 541A, the first comparator 541B, a second peak hold circuit 542A, and the second comparator 542B.

The first peak hold circuit 541A holds the positive peak value of the voltage Vx of the point X. The first comparator 541B compares the positive peak value of the point X with a predetermined positive reference voltage, and if the positive peak value of the point X exceeds a second positive reference voltage, the first comparator 541B turns on the FET Q1. Then, the resistor R5 is short-circuited. That is, R5 can be removed from equation (2), and therefore, the voltage Vc1 in equation (1) will be expressed as follows.

$$Vc1=-Vy1 \times (R7/R6) \qquad (5)$$

Therefore, the absolute value of the voltage Vc1 is increased, and accordingly the current α is increased. As a result, the output voltage Vc of the operational amplifier U2B is decreased.

Similar to the above, the second peak hold circuit 542A holds the negative peak value of the voltage Vx of the point X. The second comparator 542B compares the negative peak value of the point X with a second negative reference voltage, and if the negative peak value of the point X becomes less than the negative reference voltage, the second comparator 542B turns on the FET Q2. Then, the resistor R19 is short-circuited. That is, R19 can be removed from equation (4), and the voltage Vc3 is expressed as follows.

$$Vc3=-Vy2 \times (R7/R20) \qquad (6)$$

Therefore, the absolute value of the voltage Vc3 is increased, and accordingly the current β is increased. As a result, the output voltage Vc of the operational amplifier U2B is decreased.

In summary, when the voltage Vx at the point X is within a predetermined range (which is defined by the first positive reference voltage and the second positive reference voltage), the output voltage Vc is equal to Vc2 since voltage Vc1 and Vc2 are both zero. If the voltage Vx exceeds the range defined by the first negative reference voltage and the first positive reference voltage, but greater than the second negative reference voltage or less than the second positive reference voltage described above, the output voltage Vc is expressed by equation (1), and at this stage voltages Vc1, Vc2 and Vc3 are respectively expressed by equations (2), (3) and (4). Further, if the voltage Vx becomes greater than the second positive reference value, or less than the second negative reference value, the output voltage Vc is expressed by equation (1), and in this case, voltage Vc1, Vc2 and Vc3 are expressed by equations (5), (3) and (6), respectively. Therefore, the gain of the amplifier 53 varies in accordance with the voltage Vx which changes proportional to the change of the output voltage of the CCD 51.

It should be noted that the period of time during which the peak hold circuit 541A holds the peak value of voltage Vx corresponds to time constants determined by the resistor R25 and the condenser C2. Similarly, the period of time during which the peak hold circuit 542A holds the peak value of voltage Vx corresponds to time constants determined by the resistor R29 and the condenser C3. In this embodiment, both of the time constants are set to 1/30 seconds, which corresponds to one image frame period. The time constants can be changed by changing values of the resistors and condensers.

Further, in this embodiment, reference voltages for each of the circuits 53, 53b, 541B, and 542B can be changed. Accordingly, the characteristics of the gain of the amplifier 53 as shown in FIG. 6 can be arbitrarily set.

Figure 6:
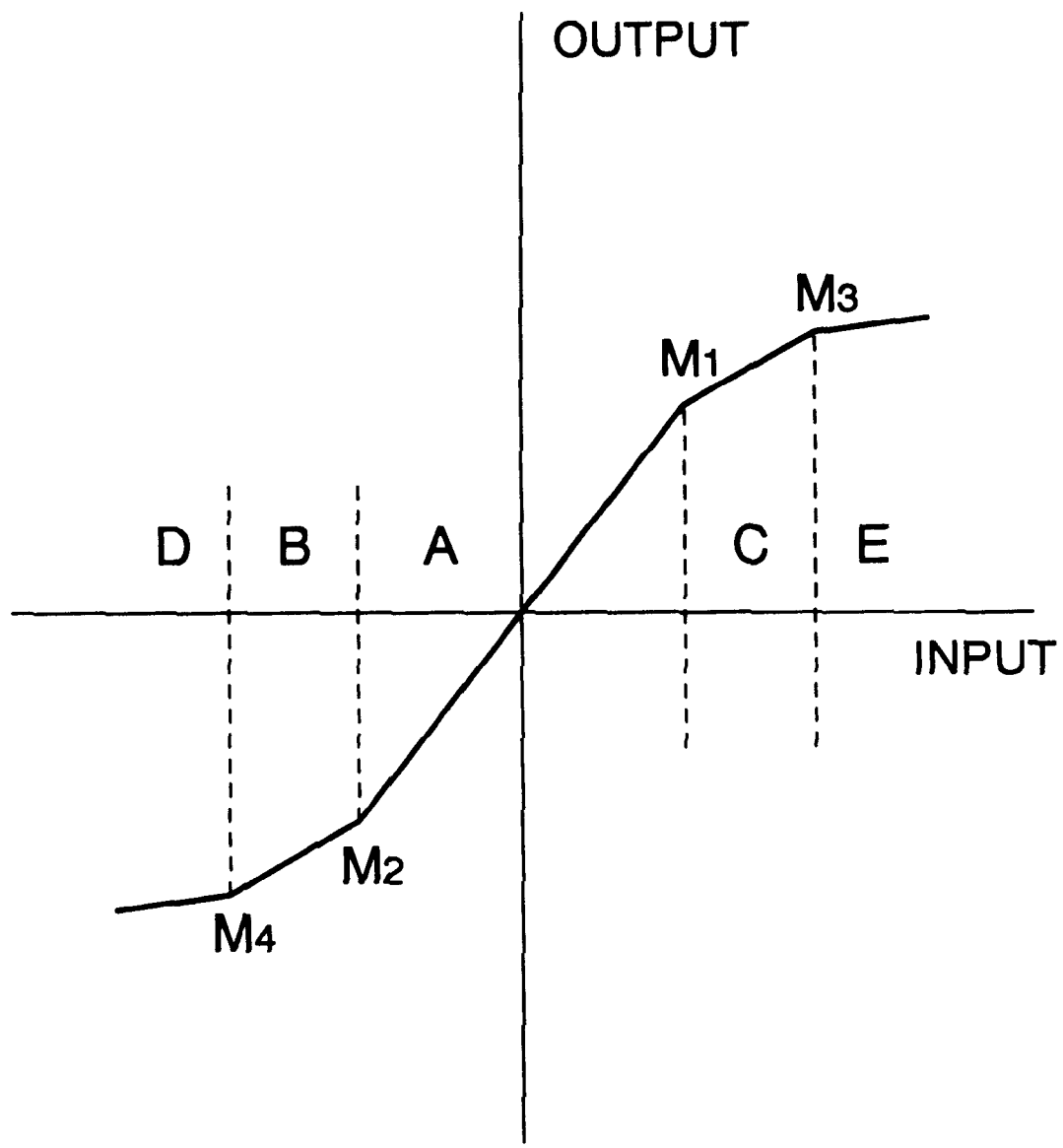
FIG. 6 shows I/O characteristics of an amplifier when gain control is performed.

FIG. 6 shows an example of an I/O (Input/Output) characteristic of the amplifier 53 when the gain thereof is controlled by the AGC 54. The CCD 51 outputs voltage which varies either a negative or a positive side with respect to zero volt. As shown in FIG. 6, when the input voltage is within a range A (i.e., when the absolute value of the input voltage is relatively small), the gain of the amplifier 53 is relatively great, while when the input voltage is out of the range A, and in a range B or C (i.e., when the absolute value of the input voltage is relatively great), the gain of the amplifier 53 is lowered. Further, when the input voltage is in a range D or E, the gain of the amplifier 53 is much lower. In this example, there are five ranges of input voltage, and the gain of the amplifier 53 corresponding to the ranges B and C are substantially the same, and the gain of the amplifier 53 corresponding to the ranges D and E are substantially the same. It may be possible to use a different number of input voltage ranges, and various gains corresponding to the respective ranges.

For example, in the output voltage control circuit 54A shown in FIG. 4A, by changing the voltage VR2, the input voltage at which the output voltage control circuit 54A starts to operate (which is represented by point M1 in FIG. 6) can be changed. Similarly, in the output voltage control circuit 54B, by changing the voltage VR18, the input voltage at which the output voltage control circuit 54B starts to operate (which is represented by point M2 in FIG. 6) can be changed. Further, in the first comparator 541B, by changing the reference voltage applied to the non-inverting terminal of the operational amplifier U4A, the peak value of the voltage Vin at which the FET Q1 is switched between ON and OFF (which is represented by point M3 in FIG. 6) can be changed. Similarly, in the first comparator 542B, by changing the reference voltage applied to the non-inverting terminal of the operational amplifier U4B, the peak value of the voltage Vin at which the FET Q2 is switched between ON and OFF (which is represented by point M4 in FIG. 6) can be changed.

Operation of the endoscope system according to the first embodiment will be described.

Firstly, the insertion portion 11 of the endoscope 10 is inserted in a human cavity, and the distal end of the insertion portion 11 is located closely adjacent to an object to be observed.

When a normal image is observed, the filter 22 is retracted from the optical path, and the mirror 32 is also retracted from the optical path.

The lamp 21 emits a white light, which is directed through the light guide fiber bundle 17 and the window 19, and is projected on the object, i.e., the organic tissues. The organic tissues reflect the light which is incident, through the window 18, on the objective optical system 15. The objective optical system 15 converges the reflected light to form an image which is guided through the image guide fiber bundle 14 and the eyepiece lens 16 and directed to the imaging unit 30. Then, via the eyepiece lens 16 and the imaging lens 30a, an image of the object is formed on the light receiving surface of the CCD camera 31. The CCD camera 31 captures the image, and outputs a video signal which is transmitted to the display device 50 through the switching device 40.

When the fluorescent image is observed, the filter 22 and the mirror 32 are inserted in the optical paths. The white light emitted by the lamp 21 passes through the filter 22, and accordingly only the excitation light is transmitted by the light guide fiber bundle 13 and emitted to the object through the window 19. The object (i.e., the organic tissues) fluoresces when the excitation light is projected. The fluorescent light emitted by the organic tissues is directed through the window 18, to the objective optical system 15 and converged thereby. The light is then directed, by the image guide fiber bundle 14, to the imaging unit 30 through the eyepiece lens 16.

In the imaging unit 30, the fluorescent light emerged from the eyepiece lens 16 is reflected by the mirror 32, and a part of the light having a wavelength within a range of 500 nm through 570 nm is reflected by the dichroic mirror 33. Thus, on the image receiving surface of the image intensifier 34, the fluorescent image is formed. The image intensifier 34 amplifies the intensity of light forming the fluorescent image, which is incident on the CCD camera 41 through the imaging optical system.

The image signal is transmitted from the CCD 51 of the CCD camera 41 to the amplifier 53 and the AGC 54. As described above, the AGC 54 controls the gain of the amplifier 53 in accordance with the characteristic shown in FIG. 6. Therefore, if the distance between the distal end of the insertion portion 11 and the object is closer to an appropriate distance and/or if the amount of the excitation light projected to the object is greater than an appropriate amount, the gain of the amplifier 53 is controlled to lower. On the other hand, if the distance between the distal end of the insertion portion 11 and the object is further to an appropriate distance and/or if the amount of the excitation light projected to the object is less than an appropriate amount, the gain of the amplifier 53 is controlled to increase. The fluorescent image signal thus processed is converted in to the video signal (e.g., the NTSC signal) by the video signal conversion circuit 55, and supplied to the switching device 40.

The switching device 40 then transmits the video signals received from the CCD camera 41 to the display device 50 for displaying the fluorescent image (image formed by the fluorescent light).

Then, an observer can observe the fluorescent image displayed by the display device 50, and determines whether the objective organic tissues have a disorder.

Figure 7:
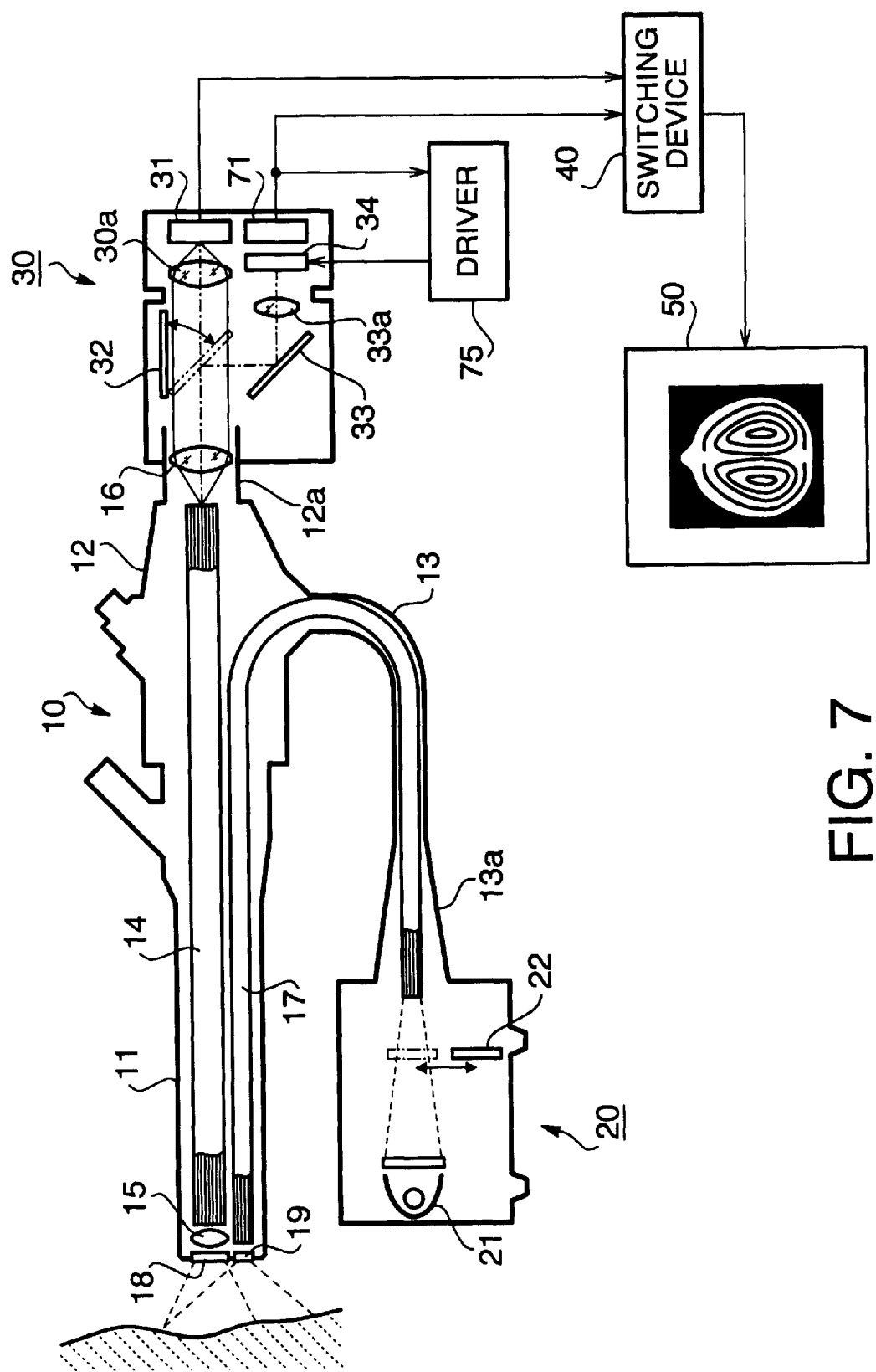
FIG. 7 shows a schematic structure of an endoscope system according to a second embodiment of the invention.

FIG. 7 shows a schematic structure of an endoscope system according to a second embodiment. The difference between the first and second embodiment is that, the CCD camera 41 of the first embodiment is replaced with a CCD camera 71, and further a driver 75 is added in the second embodiment. The other portions of the endoscope system shown in FIG. 7 are the same as those of the endoscope system shown in FIG. 1.

Figure 8:
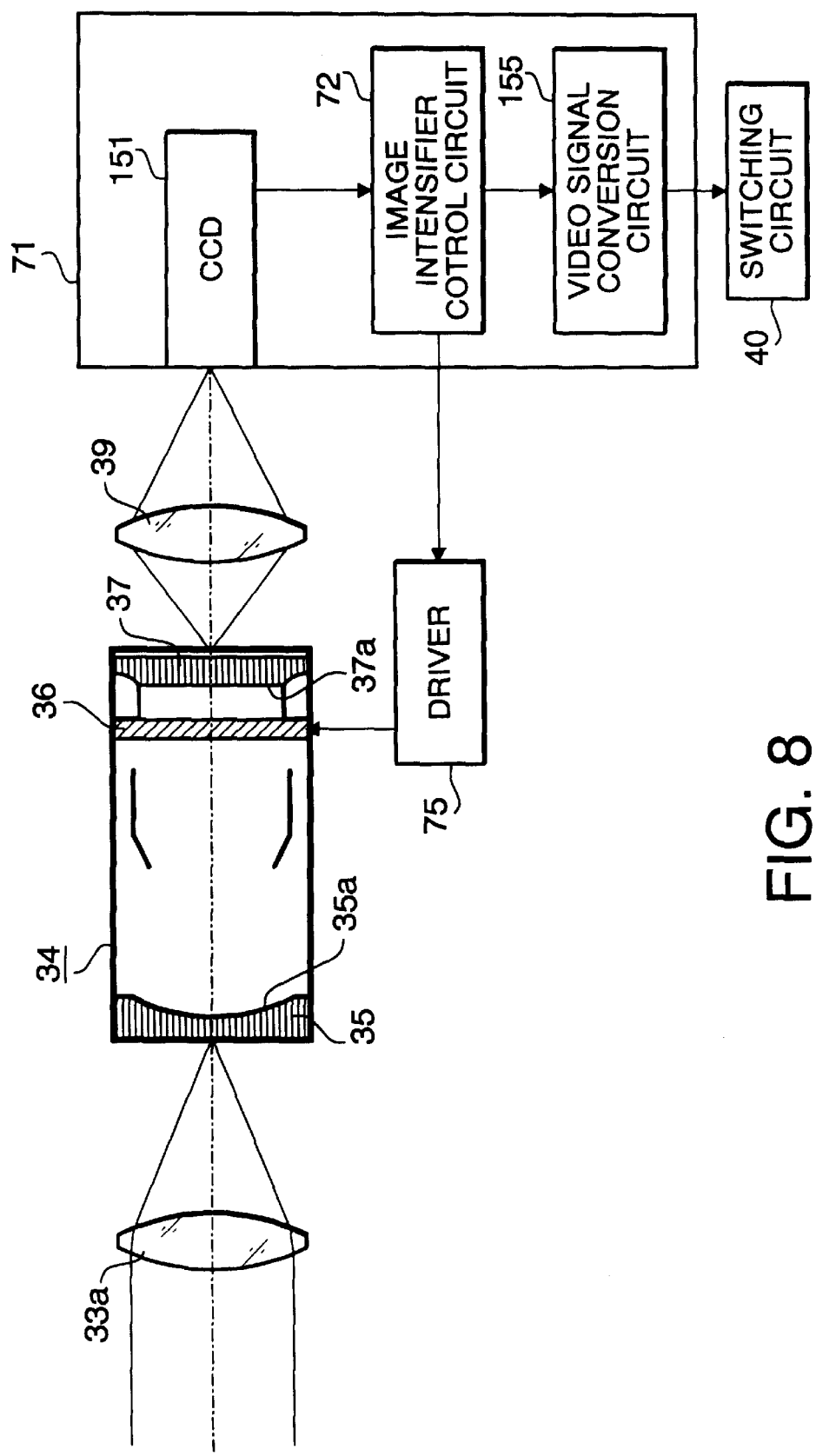
FIG. 8 schematically shows a structure of an image intensifier and a CCD camera unit according to the second embodiment.

Specifically, as shown in FIG. 8, the CCD camera 71 includes a CCD 151 which is similar to the CCD 51 of the first embodiment, an image intensifier control circuit 72, and a video signal conversion circuit 155 which is similar to the video signal conversion circuit 55. It should be noted that, in this embodiment, the image intensifier control circuit has a function as an amplifier. The image intensifier control circuit 72 controls the driver 75 to vary the voltage applied to the electrodes of the MCP 36 in accordance with the output signal of the CCD 151.

Figure 9:
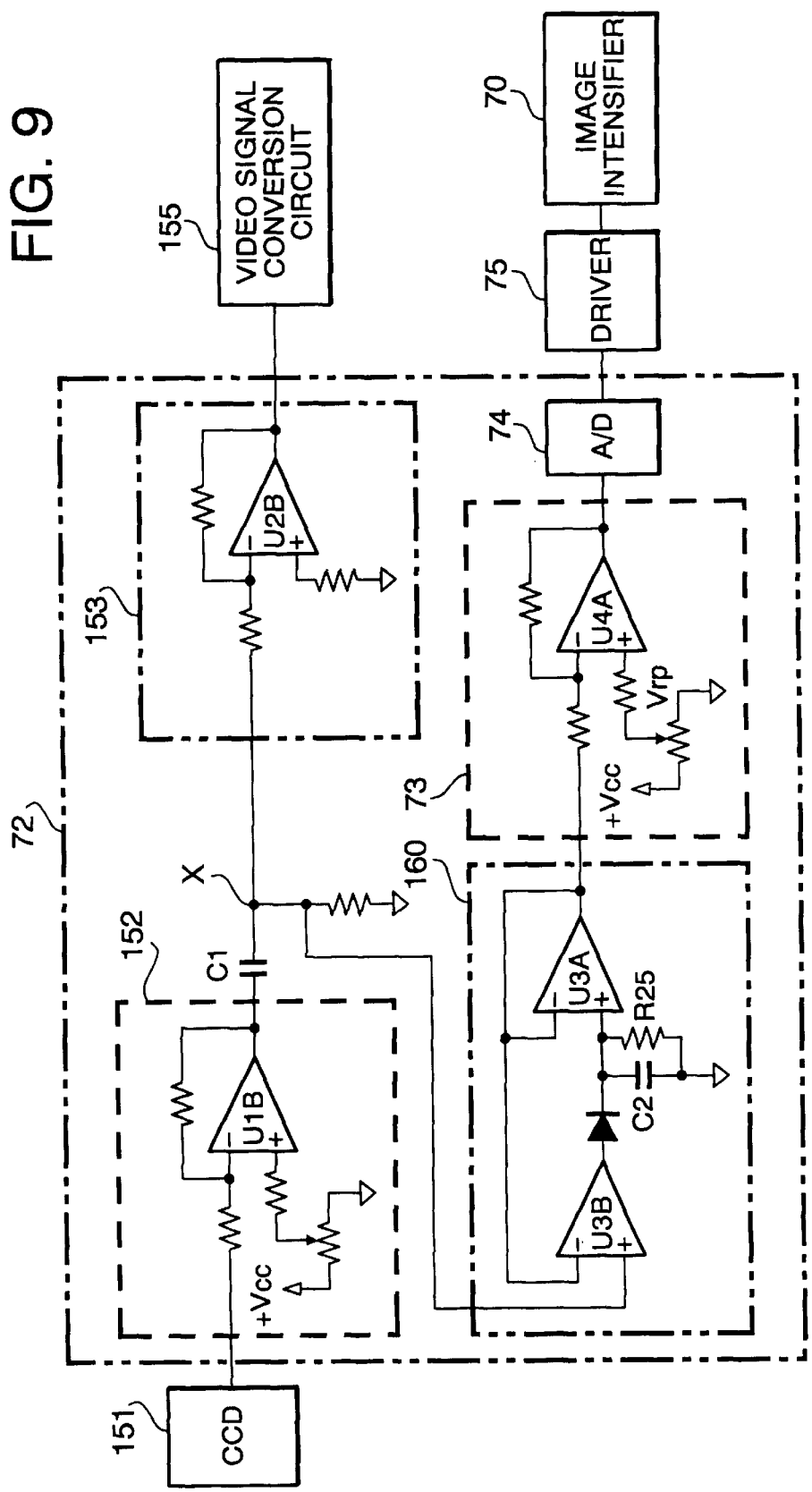
FIG. 9 shows a configuration of the image intensifier control circuit shown in FIG. 8.

FIG. 9 shows a configuration of the image intensifier control circuit 72 shown in FIG. 8.

An amplifier amplifies the output signal of the CCD 151. The DC component of the signal output by the inverting amplifier 152 is removed by a condenser C1. The output signal of the amplifier 152 is applied to another amplifier 153. The amplifier 153 amplifies the signal transmitted through the condenser C1. At a connecting point X of the condenser C1 and the amplifier 153, a peak hold circuit 160 is connected. The peak hold circuit 160 holds a positive peak value at the point X and output the same. The output value of the peak hold circuit 160 is applied to a differential amplifier 73. In the differential amplifier 73, a reference peak voltage Vrp applied to a non-inverting input terminal of an operational amplifier U4A has been adjusted such that the voltage Vrp equals to a peak voltage Vp at the point X when the distance between the object and the distal end of the endoscope 10 is appropriate, and the amount of light projected to the object is also appropriate. With the configuration, if the distance between the object and the distal end of the endoscope 10 is appropriate and the amount of light projected to the object is also appropriate, the output of the differential amplifier 73 is zero. If the distance between the object and the distal end of the endoscope 10 is too short and/or if the amount of light projected to the object is too much, the peak voltage Vp becomes greater than the reference peak voltage Vrp, and accordingly the differential amplifier 73 outputs a negative voltage. If the distance between the object and the distal end of the endoscope 10 is too long and/or if the amount of light projected to the object is insufficient, the peak voltage Vp becomes less than the reference peak voltage Vrp, and accordingly the differential amplifier 73 outputs a positive voltage. It should be noted that the condenser C1 and the resister R25 determines the time constant of the peak hold circuit 160. In this embodiment, the time constant corresponds to a period during which the CCD 151 outputs the signal for one frame.

The A/D converter 74 converts the output voltage of the differential amplifier 73 into a digital value, which is transmitted to the driver 75.

The driver 75 applies a voltage to the electrodes for the MCP 36 in accordance with the data transmitted from the A/D converter 74. Specifically, if the digital data represents the positive voltage, the driver increases the voltage applied to the MCP 36, and if the digital data represents the negative voltage, the driver decreases the voltage applied to the MCP 36. If the digital data represents zero, the driver holds the currently applying voltage.

As above, according to the embodiments, an appropriate image of the fluorescing object can be obtained, and further, the size of the imaging unit can be made compact.

By observing the normal image of the object using the CCD camera 31, and the fluorescent light image of the object using the CCD camera 41, the observer can determine the organic tissues having a disorder accurately.

The present disclosure relates to subject matter contained in Japanese Patent Application No. HEI 09-53622, filed on Mar. 7, 1997, which is expressly incorporated herein by reference in its entirety.

What is claimed is:

1. An endoscope system for observing a fluorescent image, comprising:

an endoscope unit which emits an excitation light to an object to be observed and receives a fluorescent light emitted by said object;

a filtering optical element, which extracts a predetermined color component of said fluorescent light received by said endoscope unit;

an image capturing device, which receives an image formed by said predetermined color component of said fluorescent light and outputs an image signal;

a variable gain amplifier, a gain of which changes in accordance with said image signal output by said image capturing device;

said variable gain amplifier comparing said image signal output by said image capturing device with a plurality of reference values defining a plurality of signal level ranges;

said gain of said variable gain amplifier being changed stepwisely in accordance with a signal level range in which said image signal is included;

said variable gain amplifier comprising a first amplifying circuit which amplifies said output signal of said image capturing device and outputs a first output signal, said first output signal fluctuating with respect to a predetermined value;

a second amplifying circuit which amplifies said first output signal at a predetermined gain and outputs a second output signal;

a first circuit which prepares said first output signal with a first higher reference value which is higher than said predetermined value, said first circuit lowering said gain of said second amplifying circuit if said first output signal has a higher value than said first higher reference value; and a second circuit which compares said first output signal with a first lower reference value which is lower than said predetermined value, said second circuit lowering said gain of said second amplifying circuit if said first output signal has a lower value than said first lower reference value.

2. The endoscope system according to claim 1, wherein said variable gain amplifier further comprises:

a third circuit which compares said first output signal with a second higher reference value which is higher than said first higher reference value, said third circuit further lowering said gain of said second amplifying circuit if said first output signal has a higher value than said second higher reference value; and a fourth circuit which compares said first output signal with a second lower reference value which is lower than said first lower reference value, said fourth circuit lowering said gain of said second amplifying circuit if said first output signal has a lower value than said second lower reference value.

3. The endoscope system according to claim 1, wherein said predetermined component is a light having a wavelength within a range of 500 nm through 570 nm.

4. The endoscope system according to claim 1, further comprising a display device which displays said image of a fluorescing object.

5. The endoscope system according to claim 1, further comprising an image intensifier provided in front of said image capturing device which amplifies an intensity of received light.

* * * * *